United States Patent
Kann (10) Patent No.: US 9,961,436 B2
(45) Date of Patent: May 1, 2018

(54) HEADSET COMPRISING HEART RATE MEASUREMENT UNIT

(71) Applicant: GN Audio A/S, Ballerup (DK)

(72) Inventor: Peter Ulrik Kann, Ballerup (DK)

(73) Assignee: GN AUDIO A/S (DK)

( * ) Notice: Subject to any disclaimer, the term of this patent is extended or adjusted under 35 U.S.C. 154(b) by 0 days. days.

(21) Appl. No.: 15/373,935

(22) Filed: Dec. 9, 2016

(65) Prior Publication Data

US 2017/0171658 A1  Jun. 15, 2017

(30) Foreign Application Priority Data

Dec. 11, 2015 (EP) ..................................... 15199568

(51) Int. Cl.
*H04R 25/00* (2006.01)
*H04R 1/10* (2006.01)
*A61B 5/02* (2006.01)

(52) U.S. Cl.
CPC ............. *H04R 1/1091* (2013.01); *A61B 5/02* (2013.01); *H04R 1/105* (2013.01); *H04R 1/1066* (2013.01); *H04R 1/1016* (2013.01)

(58) Field of Classification Search
CPC  H04R 1/1066; H04R 1/1016; H04R 2420/07; H04R 1/1008; H04R 1/1041
USPC .......................................... 381/74, 380, 374
See application file for complete search history.

(56) References Cited

U.S. PATENT DOCUMENTS

| | | | |
|---|---|---|---|
| 4,791,673 A | 12/1988 | Schreiber | |
| 7,209,775 B2 | 4/2007 | Bae et al. | |
| 8,180,090 B2 | 5/2012 | Hupkes | |
| 8,335,334 B1 * | 12/2012 | Luna Rosas | H04R 1/105 381/370 |
| D695,265 S * | 12/2013 | Schaal | D14/205 |
| 8,647,270 B2 | 2/2014 | LeBoeuf et al. | |
| 8,655,004 B2 | 2/2014 | Prest et al. | |
| 8,737,667 B2 | 5/2014 | Oh et al. | |
| 8,989,830 B2 | 3/2015 | Leboeuf et al. | |
| 9,002,420 B2 | 4/2015 | Pattikonda et al. | |
| 2003/0233051 A1 * | 12/2003 | Verjus | A61B 5/02438 600/528 |
| 2006/0177087 A1 * | 8/2006 | Ham | H04R 1/105 381/381 |

(Continued)

FOREIGN PATENT DOCUMENTS

| | | |
|---|---|---|
| GB | 2524334 | 9/2015 |
| WO | WO 2015/026043 | 2/2015 |

OTHER PUBLICATIONS

European Search Report dated Jul. 5, 2016 for European patent application No. 15199568.5.

*Primary Examiner* — Matthew Eason
*Assistant Examiner* — Julie X Dang
(74) *Attorney, Agent, or Firm* — Altera Law Group, LLC (57) ABSTRACT

Disclosed are an earpiece and a headset comprising an earpiece, where the earpiece is configured to be arranged at least partly in an ear of a user. The earpiece comprising a heart rate measurement unit for measuring the heart rate in/at the ear of the user; a receiving member configured for accommodating and/or receiving a detachable speaker unit of the headset; and a detachable speaker unit which is configured to be inserted and/or attached and removed and/detached from the receiving member of the earpiece.

15 Claims, 6 Drawing Sheets

(56) References Cited

U.S. PATENT DOCUMENTS

| | | | |
|---|---|---|---|
| 2007/0133836 A1* | 6/2007 | Lee | H04M 1/05 381/370 |
| 2008/0279409 A1 | 11/2008 | Hupkes | |
| 2008/0298613 A1* | 12/2008 | Slamka | H04M 1/05 381/311 |
| 2009/0010461 A1* | 1/2009 | Klinghult | A61B 5/0002 381/309 |
| 2009/0041284 A1* | 2/2009 | Tanaka | H04R 1/1016 381/370 |
| 2009/0097689 A1 | 4/2009 | Prest et al. | |
| 2009/0105548 A1* | 4/2009 | Bart | A61B 5/02438 600/300 |
| 2012/0163616 A1* | 6/2012 | Birch | H04M 1/6058 381/74 |
| 2012/0243723 A1* | 9/2012 | Halkosaari | H04R 1/1066 381/379 |
| 2014/0211959 A1 | 7/2014 | Boyajian et al. | |
| 2014/0328492 A1 | 11/2014 | Feeley et al. | |
| 2015/0092972 A1 | 4/2015 | Lai et al. | |
| 2015/0181325 A1* | 6/2015 | Urup | H04R 1/1091 381/74 |
| 2015/0245127 A1* | 8/2015 | Shaffer | H04R 1/1025 381/380 |

\* cited by examiner

HEADSET COMPRISING HEART RATE MEASUREMENT UNIT

FIELD

The present disclosure relates to a headset comprising a first earpiece. The earpiece is configured to be arranged in an ear of a user. The earpiece comprises a heart rate measurement unit for measuring the heart rate in and/or at the ear of the user.

BACKGROUND

U.S. Pat. No. 9,002,420 BB discloses a watch worn by a user for interfacing with a mobile communication device. The watch includes an electronic display worn by user. The electronic display includes an interface for wirelessly interfacing with a mobile communication device carried by the user. The user interfaces with the electronic display to perform operations upon the mobile communication device. The watch also includes a mechanism to wirelessly establishing a voice channel with the mobile communication device for performing operations upon the mobile communication device. Additionally, the watch includes a mechanism for projecting directional sound to the user.

U.S. Pat. No. 8,655,004 BB discloses a monitoring system that can be placed proximate to the head or ear of a user. According to one embodiment, the monitoring system can be used with headphones, earbuds or headsets. The monitoring system can, for example, be used to monitor user activity, such as during exercise or sporting activities. The positioning of the monitoring system can also facilitate sensing of other user characteristics (e.g., biometric data), such as temperature, perspiration and heart rate. The monitoring system can also be used to control an electronic device. In one embodiment, the monitoring system facilitates user control of the electronic device using head gestures.

SUMMARY

There is a need for an improved headset comprising an earpiece with heart rate measurement means.

Disclosed is a headset comprising a first earpiece. The earpiece is configured to be arranged at least partly in an ear of a user. The earpiece comprises a heart rate measurement unit for measuring the heart rate in and/or at the ear of the user. The earpiece comprises a receiving member configured for accommodating and/or receiving a detachable speaker unit of the headset. The earpiece comprises a detachable speaker unit which is configured to be inserted and/or attached and removed and/or detached from the receiving member of the earpiece.

Also disclosed is an earpiece for use in a headset. The earpiece is configured to be arranged at least partly in an ear of a user. The earpiece comprises a heart rate measurement unit for measuring the heart rate in and/or at the ear of the user. The earpiece comprises a receiving member configured for accommodating and/or receiving a detachable speaker unit of the headset. The earpiece comprises a detachable speaker unit which is configured to be inserted and/or attached and removed and/or detached from the receiving member of the earpiece.

At least a part of the earpiece, such as the whole earpiece, is configured to be arranged in the ear, such as in the concha of the ear. The earpiece can be retained in the ear by different means, such as by the use of an earwing, by use of an earhook etc. The earhook may be a part of the headset and/or earpiece, and the earhook may be arranged at least partly behind the ear. All other parts of the earpiece, i.e. except the earhook, may be arranged in the ear of the user.

Measurement of the heart rate or pulse of the user can be provided by measuring the heart rate of the user in and/or at the ear of the user, such as in the outer ear, such as in the ear canal, such as in the concha of the ear, such as in the pinna, such as behind the ear, such as at the ear lobe, such as on the front of the ear etc.

It is desirable for users to measure their heart rate for example when performing physical exercise such as sports activities. Thus the headset may be a headset suitable for use in sports activities, such as a headset which is robust, water resistant, dirt resistant, sweat resistance and/or suitable for outdoor use.

It is an advantage that the earpiece comprises a receiving member configured for accommodating and/or receiving a detachable speaker unit of the headset. Further it is an advantage that the earpiece comprises the detachable speaker unit which is configured to be inserted and/or attached and removed and/or detached from the receiving member of the earpiece. Thus the speaker unit is detachable or removable. The speaker unit may comprise a transducer. The speaker unit may comprise a processing unit or processor. The earpiece, e.g. a housing of the earpiece, may comprise a processing unit. The processing unit(s) may be provided on (a) printed circuit board(s).

It is an advantage that the speaker unit is detachable as this allows the user to use the headset either with or without the speaker unit.

With the speaker unit in the earpiece the user can listen to for example music and/or radio through the speaker unit while performing for example the sports activity and measuring the heart rate, and/or talking on the phone using the speaker unit to hear the conversation partner in the other end of the line.

Without the speaker unit the user can for example use the headset for measuring his/her heart rate for example when performing sports activities without listening to music and/or radio. When the speaker unit is removed from the earpiece the user can get (fresh) air to his/her ear for example if the earpiece comprises a through hole for receiving the detachable speaker unit. This may be advantageous for the user if he/she performs heavy activity producing a lot of heat. Further, when the speaker unit is removed from the earpiece the user can better hear the surroundings, such as other people's voices, for example if the user is performing the sports activities together with other people, and/or such as the natural sounds of the surroundings, such as bird song in a forest if the user for example is running in the forest.

Thus it is an advantage that the speaker unit is detachable, as this allows the user to easily shift between having the speaker unit attached or detached from the earpiece depending on what suits the user best in the certain circumstances. As the attachment and detachment of the speaker unit should be easy, the user can bring the speaker unit along in for example a pocket of his/her clothes and quickly attach the speaker unit in the earpiece when needed, for example if the user suddenly needs to perform a phone call using his/her mobile phone, then the headset can be connected, such as wirelessly or wired, with the mobile phone for reproducing the audio signals of the phone conversation.

Likewise the speaker unit can be attached in the earpiece for the user to listen to for example music, and if the user at a time does not want to have the speaker unit attached in the earpiece anymore for example because he/she needs to speak to a person performing the sports activity together with the user, the user can quickly and easily detach the speaker unit from the earpiece and put the speaker unit in for example a pocket of his/her clothes.

The headset may also comprise a printed circuit board and/or a battery and/or a transceiver for wireless communication, such as a Bluetooth transceiver for communication with a transceiver in a mobile phone, in a tablet, in a pc etc., such as for communicating the measured heart rate data to an application or app or program in the mobile phone, tablet or pc. The printed circuit board and/or a battery and/or a transceiver may be arranged in the earpiece of the headset, and/or in a housing of the headset, such as a housing configured to be arranged behind the ear of the user, and/or in the detachable speaker unit. If one or more of the printed circuit board and/or the transceiver is arranged in the detachable speaker unit, the headset may comprise a logging unit for logging the data of the heart rate measurement unit, if the speaker unit is detached from the earpiece. When the speaker unit is attached in the earpiece again, the heart rate measurement data can be transmitted or sent to the mobile phone, tablet, pc etc.

The detachable speaker unit may be shaped as a disk having a volume, such as a disk having a diameter and a thickness or height, where the thickness may be smaller than the diameter, or where the thickness may be larger than the diameter, or where the thickness and the diameter are substantially or about the same size or length. The thickness of the disk may vary along its length, for example the disk may be thicker in its centre than at its boundary, or the disk may be thicker it its boundary than at its centre.

The detachable speaker unit may be shaped as a sphere or a ball defined by its diameter.

The detachable speaker unit may be shaped as a plate or slab defined by its length, width and/or height. The height may vary along the length and/or width of the plate or slab. The length and/or width may vary.

The detachable speaker unit may be defined by its outer surface which is configured to at least partly fit or match or correspond to the surface of the receiving member, such as the inner surface of the receiving member. At least a part of the outer surface of the speaker unit matches the inner surface of the receiving member, such as the whole outer surface of the detachable speaker unit or a part of the outer surface of the detachable speaker unit.

At least a part of the outer surface of the speaker unit is configured to be attached in at least a part of the receiving member. For example if the speaker unit is shaped as a disk, then the part of the disk represented by its thickness may be the part of the outer surface of the speaker unit which is configured to be touching or held in the receiving member. Another part of the speaker unit, such as the part of the speaker unit represented by its diameter may be configured to not be touching the receiving member.

In some embodiments the receiving member comprises a through hole. Thus in this case the user can get air to his ear and hear the surroundings better when the speaker unit is detached.

In some embodiments the receiving member comprises a recess. In this case there may not be a through hole in the earpiece but a recess instead. When the speaker unit is detached, the earpiece and thus the headset weight less and thus be lighter to wear than when the speaker unit is attached.

In some embodiments the receiving member comprises a membrane. The membrane may comprise a sheet, a plate with holes, a foam, a fabric, a cloth etc. The membrane may be arranged in the receiving member, such as in the through hole, such that the membrane covers the access to the ear canal to avoid that dirt and/or water and/or sweat enters the ear canal. The membrane should allow air and sound to enter the ear canal. The membrane can be made of a fabric such as the brand Gore-Tex.

In some embodiments the receiving member is circular and/or the speaker unit is circular and/or the inner diameter or circumference of the receiving member matches the outer diameter or circumference of the speaker unit. Alternatively and/or additionally the receiving member, such as the inner surface of the receiving member, and the speaker unit, such as the outer surface of the speaker unit, may the curved and/or elliptical and/or round. The speaker unit may be shaped as a disk or as a ball or sphere. A first element of the outer surface of the speaker unit may be the outer surface where the distance to the centre of mass of the speaker unit is largest, i.e. larger than the distances of all the other elements of the outer surface to the centre of mass of the speaker unit, such as a second element of the outer surface of the speaker unit.

The inner diameter or circumference of the receiving member may match or fit or correspond to the outer diameter or circumference of the speaker unit such that the speaker unit exactly fit in the receiving member, such as fitting in the through hole.

In some embodiments an inner surface of the receiving member comprises one or more first electrical connection parts and/or an outer surface of the speaker unit comprises one or more second electrical connection parts, and/or the first electrical connection parts and the second electrical connection parts are configured to be arranged opposite and/or facing each other, when the speaker unit is inserted and/or attached in the receiving member thereby providing an electrical connection between the speaker unit and the earpiece. Hereby an electrical connection between the speaker unit and the earpiece can be obtained. The electrical connections or electrical parts may be termed terminals.

In some embodiments at least two of the one or more first electrical connection parts and at least two of the one or more second electrical connection parts, respectively, are arranged to be rotationally symmetrical. It is an advantage that it is easier to attach the speaker unit in the receiving member due the rotational symmetry of the arrangement of the connections parts in the speaker unit and in the receiving member, respectively.

For example two connection parts may be arranged with an angle of 180 degrees relative to each other, or three connection parts may be arranged with an angle of 120 degrees relative to each other, or four connection parts may be arranged with an angle of 90 degrees relative to each other etc. The number of first connection parts should be equal to the number of second connections parts.

In some embodiments the one or more first electrical connection parts and/or the one or more second electrical connection parts are shaped as a circle/ring or part of a circle/ring. Thus as an alternative to the connection parts being shaped as single points or terminals, the first connection parts may extend along at least a part of the receiving member, such as the inner surface of the receiving member, and/or the second connection parts may extend along at least a part of the outer surface of the speaker unit. It is an advantage that the user does not need to be very precise with the orientation of the speaker unit relative to the receiving member when attaching the speaker unit in the receiving member, as the first connection parts extending for example all the way or half-way around the inner surface of the receiving member and/or the second connection parts extending for example all the way or half-way around the outer surface of the speaker unit provides that the electrical connection can be obtained in many different configurations as the first connections parts are easier to align with the second connections part when not all the connection parts are smaller points, but some of the connection parts are larger rings or slabs.

Thus either both the first and the second connection parts are shaped like at least a part of circle extending around the receiving member and speaker unit, respectively. Or only the first or the second connection parts are shaped like at least a part of a circle extending around the receiving member or the speaker unit. In the last case, the other connection part, i.e. the one or more second electrical connections parts or the one or more first electrical connections parts, respectively, may be shaped as points or dots or terminals.

In some embodiments the surface of the earpiece defining the receiving member, also called inner surface of receiving member, comprises an internal screw thread, and/or the outer surface of the speaker unit comprises an external screw thread, where the external screw thread of the speaker unit is configured to be screwed into the internal screw thread of the surface of the earpiece defining the receiving member. Thus the internal screw thread may be a female part and the external screw thread may be a male part.

In some embodiments the receiving member comprises a bayonet receptor, such as the surface of the earpiece defining the receiving member, also called inner surface of receiving member, and the outer surface of the speaker unit comprises a bayonet connector, where the bayonet connector of the speaker unit is configured to be connected and/or inserted into the bayonet receptor of the receiving member. The bayonet receptor may be female part and the bayonet connector may be a male part.

In some embodiments the inner surface of the receiving member and the outer surface of the speaker unit comprise snap-fitting components configured for snap-fitting the speaker unit into the receiving member. Snap-fitting may comprise snap-locking, press-fitting, spring-locking and/or spring-hatching.

In some embodiments the heart rate measurement unit is configured to touch and/or contact and/or adjoin the anti-tragus of the ear and/or be arranged with a constant distance to the antitragus of the ear, when the earpiece is arranged for use in the user's ear. Thus the heart measurement unit can perform the measurements of the heart rate of the user by measuring at the antitragus of the ear, such as by measuring on the skin of the antitragus and/or measuring close to the skin of the antitragus. Thus the heart rate measurement unit does not need to touch the skin for performing the measurements, it may be sufficient that the heart rate measurement unit is just close to the skin. The distance between the skin and the heart rate measurement unit should then be kept constant for allowing correct measurements.

In some embodiments the earpiece comprises an earwing unit for securing and/or retaining the earpiece in the ear of the user. Securing and/or retaining the earpiece in the ear by means of the earwing may be by means of press-fitting the earwing in the skin or folds of the ear. The earwing may be formed as an oblong component, such as a flexible oblong component.

In some embodiments the earwing is configured to touch and/or contact and/or adjoin the concha of the user's ear, such as to touch and/or contact and/or adjoin a part of the concha pointing towards and/or being closest to the top of the user's head, when the earpiece is arranged for use in the user's ear. The heart rate measurement unit and the earwing may be arranged in opposite ends of the earpiece, such as the heart rate measurement unit being arranged in a first end of the earpiece and the earwing being arranged in a second end of the earpiece.

In some embodiments the earwing is configured to point towards the top of the user's ear and/or head, and the heart rate measurement unit is configured to point towards the bottom of user's ear and/or head, when the earpiece is arranged for use in the user's ear.

In some embodiments the earwing unit is replaceable. Thus the earwing is changeable, interchangeable and exchangeable. The headset may be delivered to the user with a number of different earwing designs, such as four different earwing designs which the user can select from and thus using the earwing design which fits best in his/her ear providing a stable and comfortable fit of the earpiece.

In some embodiments at least a part of the earpiece, such as the heart rate measurement unit and/or the earwing, comprises a resilient material, such as silicone rubber. Thus at least a part of the earwing may be made from a resilient material to provide a stable, comfortable and secure fit in the ear.

In some embodiments the speaker unit comprises a replaceable eargel unit. The headset may be delivered to the user with a number of different eargel designs, such as four different eargel designs which the user can select from and thus using the eargel design which fits best in his/her ear to provide a stable, comfortable and secure fit in the ear. The eargel unit is for fitting in the ear canal, such as in the outer end of the ear canal pointing towards the outside or surroundings.

In some embodiments the headset comprises an earhook configured to be arranged at least partly around the outer ear of the user.

In some embodiments the heart rate measurement unit is arranged in a first end of the earhook configured to be arranged behind the ear of the user. Thus the first end of the earhook may be provided behind the ear when the user is wearing the earpiece of the headset. The second end of the earhook may be configured to be attached to the earpiece of the headset, i.e. the second end may be arranged in the ear and/or on the front of the ear.

In some embodiments the earpiece comprises a microphone, and the microphone may be arranged in a housing of the earpiece. The microphone can be arranged in a non-detachable part of the earpiece, such as in a housing.

In some embodiments the earpiece comprises a microphone, and the microphone may be arranged in the speaker unit. Thus in this case the microphone is arranged in the detachable speaker unit. The microphone may comprise one or more microphone units, such as two microphone units. When attaching the detachable speaker unit comprising the microphone in the receiving member care may be taken to ensure that the speaker unit is arranged or oriented in the receiving member in a way or such that the microphone is pointing in a direction to allow the speech from the user to be captured sufficiently by the microphone to transmit the speech audio signals such that the conversation partner in the other end of the phone line during a phone call can hear the user speaking. Thus the microphone may point outwards and/or downwards toward the mouth of the user when provided in the speaker unit attached in the receiving member.

In some embodiments the headset comprises a second earpiece configured to be arranged in the other ear of the user, and the first and the second earpiece may be connected by a first part of a wire. A microphone, i.e. another microphone than the microphone arranged in the earpiece, and/or a control panel may be arranged on a second part of the wire. The control panel may configured for controlling volume of music, incoming telephone calls etc. The wire may be configured to be arranged on the chest of the user such that the microphone on the wire can receive speech from the user, and/or the user can reach the control panel easily with his/her fingers. Alternatively the microphone is arranged in the earpiece as disclosed above. In this case, a wire connecting the earpiece, e.g. a first earpiece, with the second earpiece in the other end of the user, will then typically be configured to be arranged in the neck of the user, which may provide better for comfort for the user, e.g. during sports activities.

The present invention relates to different aspects including the system described above and in the following, and corresponding system parts, methods, devices, systems, networks, kits, uses and/or product means, each yielding one or more of the benefits and advantages described in connection with the first mentioned aspect, and each having one or more embodiments corresponding to the embodiments described in connection with the first mentioned aspect and/or disclosed in the appended claims.

BRIEF DESCRIPTION OF THE DRAWINGS

The above and other features and advantages will become readily apparent to those skilled in the art by the following detailed description of exemplary embodiments thereof with reference to the attached drawings, in which.

DETAILED DESCRIPTION

Various embodiments are described hereinafter with reference to the figures. Like reference numerals refer to like elements throughout. Like elements will, thus, not be described in detail with respect to the description of each figure. It should also be noted that the figures are only intended to facilitate the description of the embodiments. They are not intended as an exhaustive description of the claimed invention or as a limitation on the scope of the claimed invention. In addition, an illustrated embodiment needs not have all the aspects or advantages shown. An aspect or an advantage described in conjunction with a particular embodiment is not necessarily limited to that embodiment and can be practiced in any other embodiments even if not so illustrated, or if not so explicitly described.

Throughout, the same reference numerals are used for identical or corresponding parts.

Figure 1:
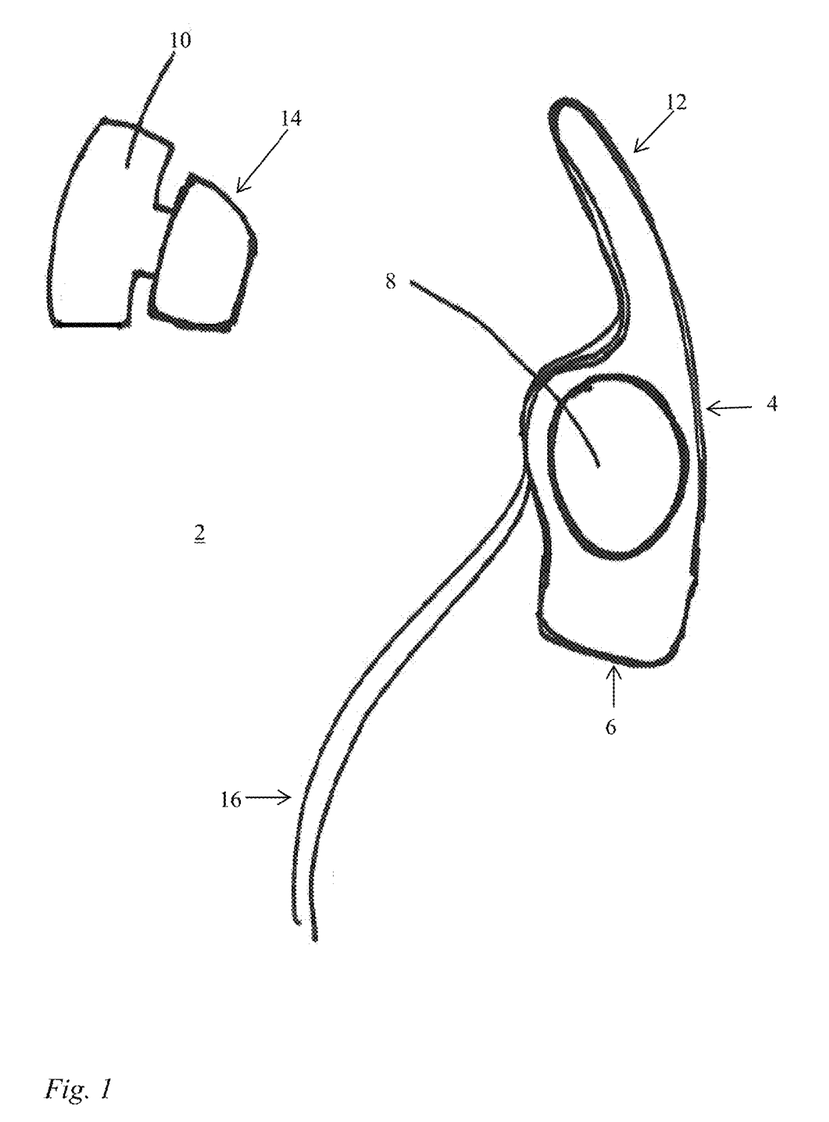
FIG. 1 schematically illustrates an example of a headset comprising a first earpiece.

FIG. 1 schematically illustrates an example of a headset 2 comprising a first earpiece 4. The earpiece 4 is configured to be arranged at least partly in an ear of a user. The earpiece 4 comprises a heart rate measurement unit 6 for measuring the heart rate in and/or at the ear of the user. The earpiece 4 comprises a receiving member 8 configured for accommodating and/or receiving a detachable speaker unit 10 of the headset 2. The earpiece 4 comprises a detachable speaker unit 10 which is configured to be inserted and/or attached and removed and/or detached from the receiving member 8 of the earpiece 4.

The earpiece 4 comprises an earwing unit 12 for securing and/or retaining the earpiece 4 in the ear of the user.

The speaker unit 10 comprises a replaceable eargel unit 14.

The earpiece 4 may comprise a wire 16 for example to connecting to a second earpiece (not shown). A microphone (not shown) and/or a control panel may be arranged on the wire 16. The wire 16 may be configured to be arranged on the chest of the user so that the microphone on the wire can receive speech from the user, and/or the user can reach the control panel easily with his/her fingers. Alternatively the wire 16 may be configured to be arranged in the neck of the user.

FIGS. 2A-2D schematically illustrates examples of the receiving member 8.

Figure 2A:
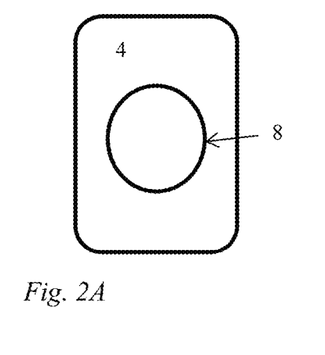
FIGS. 2A-2D schematically illustrates examples of a receiving member.

FIG. 2A shows an example where the receiving member 8 comprises a through hole.

Figure 2B:
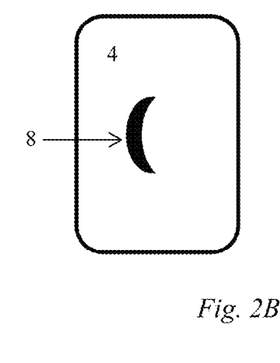

FIG. 2B shows an example where the receiving member 8 comprises a recess.

Figure 2C:
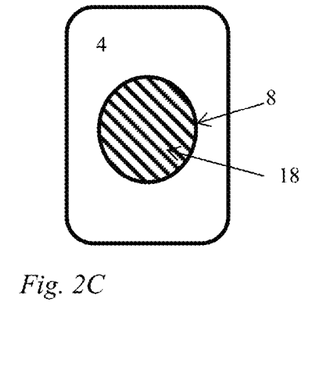

FIG. 2C shows an example where the receiving member 8 comprises a membrane 18.

Figure 2D:
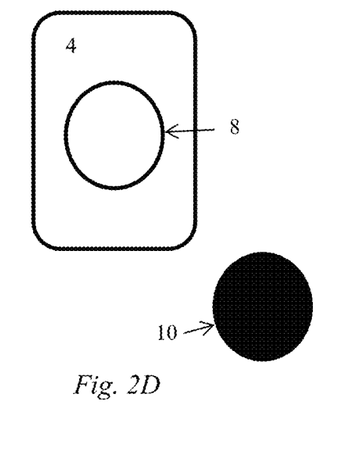

FIG. 2D shows an example where the receiving member 8 is circular and where the speaker unit 10 is circular. The inner diameter of the receiving member 8 matches the outer diameter of the speaker unit 10.

FIGS. 3A-3E schematically illustrates examples of electrical connection parts of the receiving member and the speaker unit.

Figure 3A:
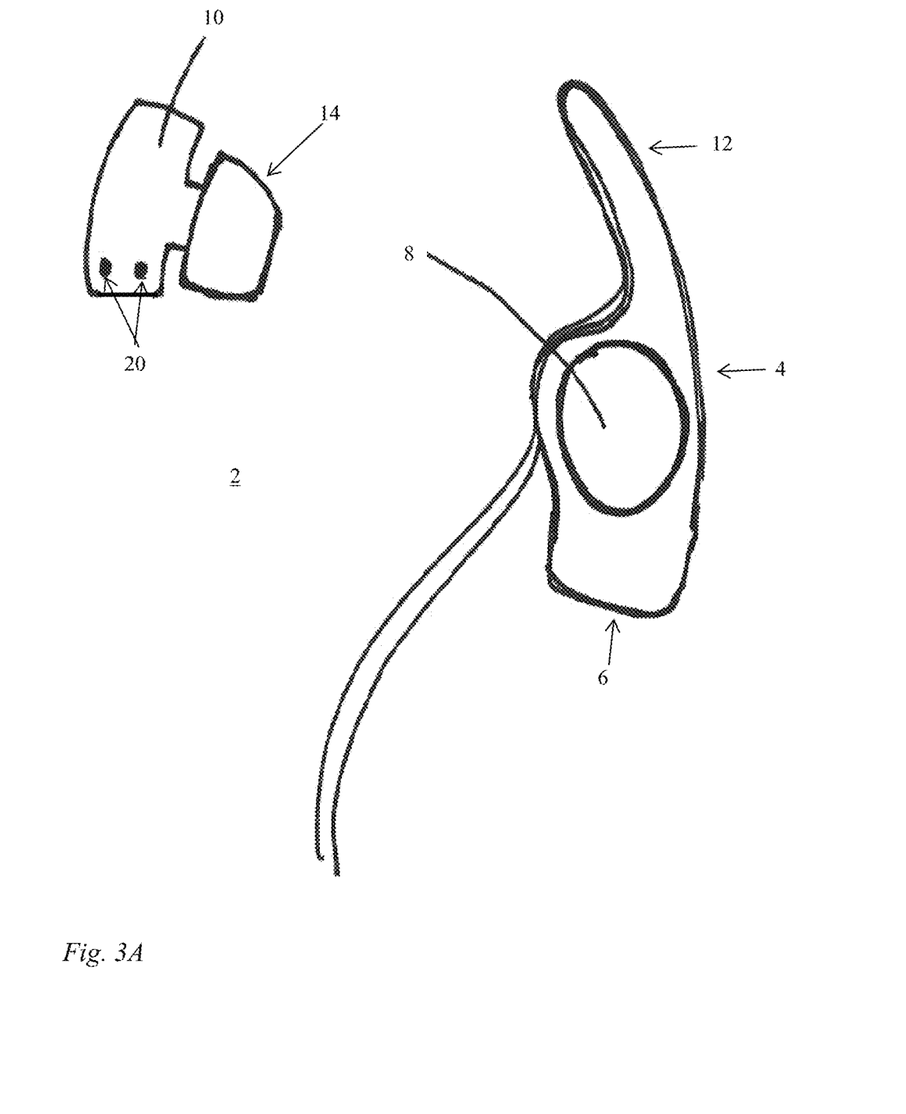
FIGS. 3A-3E schematically illustrates examples of electrical connection parts of the receiving member and the speaker unit.

FIG. 3A shows an example of a headset 2 comprising a first earpiece 4. The earpiece 4 is configured to be arranged at least partly in an ear of a user. The earpiece 4 comprises a heart rate measurement unit 6 for measuring the heart rate in and/or at the ear of the user. The earpiece 4 comprises a receiving member 8 configured for accommodating and/or receiving a detachable speaker unit 10 of the headset 2. The earpiece 4 comprises a detachable speaker unit 10 which is configured to be inserted and/or attached and removed and/or detached from the receiving member 8 of the earpiece 4.

The earpiece 4 comprises an earwing unit 12 for securing and/or retaining the earpiece 4 in the ear of the user.

The speaker unit 10 comprises a replaceable eargel unit 14.

An inner surface of the receiving member 8 comprises one or more first electrical connection parts (not shown).

An outer surface of the speaker unit 10 comprises one or more second electrical connection parts 20.

The first electrical connection parts (not shown) and the second electrical connection parts 20 are configured to be arranged opposite and/or facing each other, when the speaker unit 10 is inserted or attached in the receiving member 8 thereby providing an electrical connection between the speaker unit 10 and the earpiece 4.

Figure 3B:
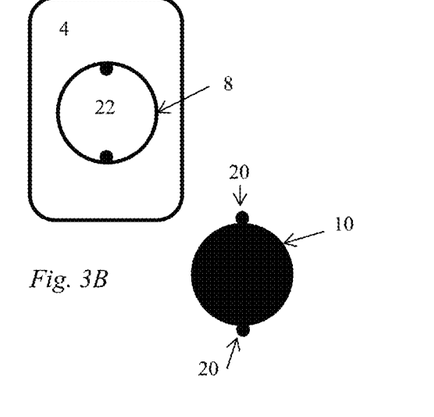
Figure 3C:
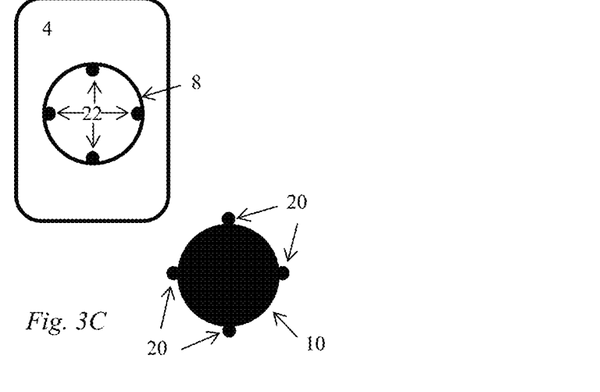

FIGS. 3B and 3C show examples where at least two of the one or more first electrical connection parts 22 of the receiving member 8 in the earpiece 4 and at least two of the one or more second electrical connection parts 20 of the speaker unit 10 are arranged to be rotationally symmetrical.

In FIG. 3B each of the speaker unit 10 and the receiving member 8 comprises two electrical connections parts 20 and 22, respectively, arranged with a distance of about 180 degrees between the two electrical connection parts.

In FIG. 3C each of the speaker unit 10 and the receiving member 8 comprises four electrical connections parts 20 and 22, respectively, arranged with a distance of about 90 degrees between each of the neighbours of the four electrical connection parts.

Figure 3D:
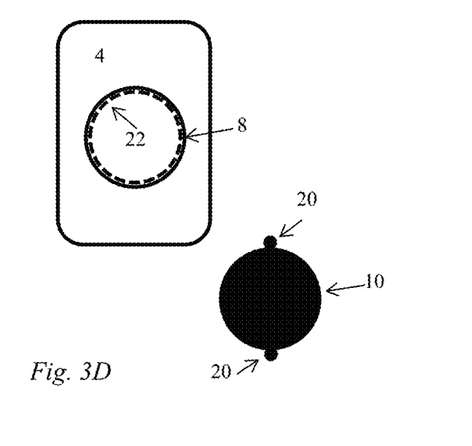

FIG. 3D shows an example where the first electrical connection part 22 of the receiving member 8 is shaped as a circle and/or ring or part of a circle and/or ring extending along the inner surface of the receiving member 8. The second electrical connection parts 20 are shaped as dots or points as in FIGS. 3A, 3B and 3C.

Figure 3E:
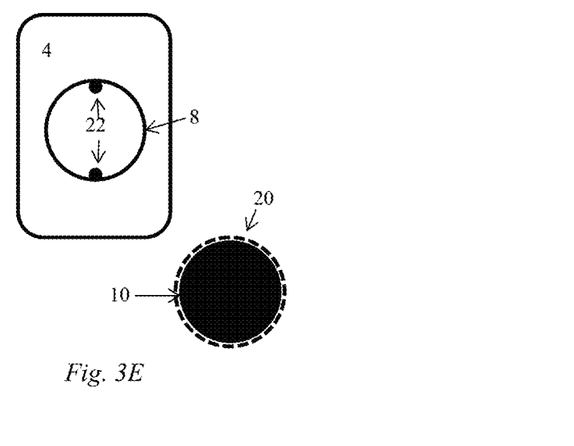

FIG. 3E shows an example where the second electrical connection part 20 of the speaker unit 10 is shaped as a circle and/or ring or part of a circle and/or ring extending along the outer surface of the speaker unit 10. The first electrical connection parts 22 are shaped as dots or points as in FIGS. 3A, 3B and 3C.

Figure 4A:
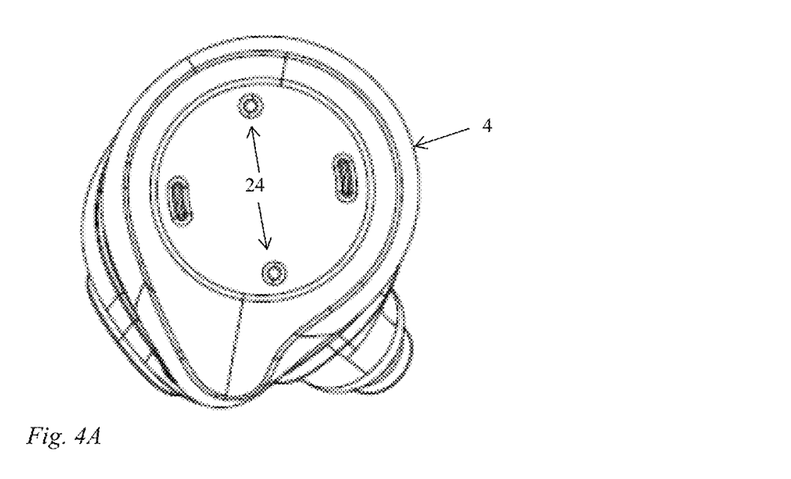
FIGS. 4A-4C schematically illustrates examples of a microphone of the earpiece.
Figure 4B:
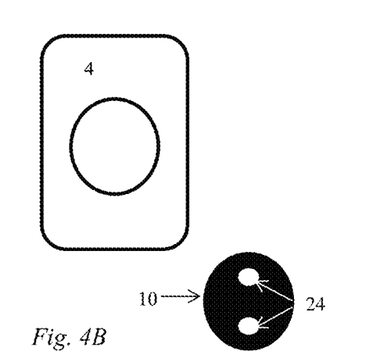
Figure 4C:
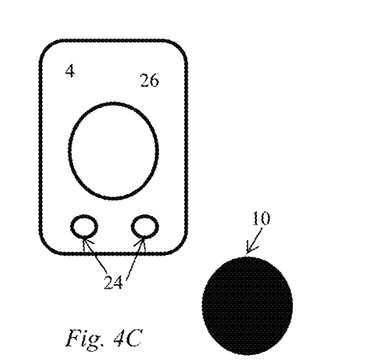

FIGS. 4A-4C schematically illustrates examples of a microphone of the earpiece.

FIG. 4A shows an example where the earpiece 4 comprises two microphones 24.

FIG. 4B shows an example where the microphones 24 are arranged in the detachable speaker unit 10.

FIG. 4C shows an example where the microphones 24 are arranged in a housing 26 of the earpiece 4.

Figure 5A:
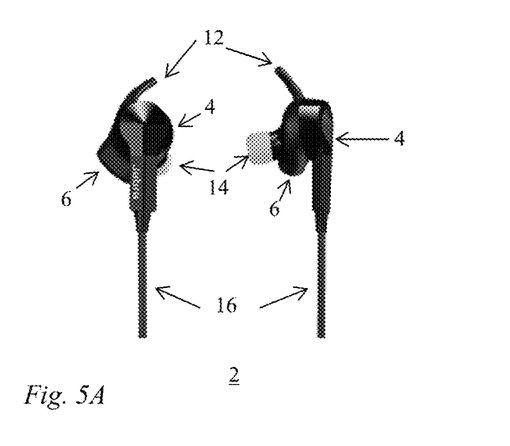
FIGS. 5A-5B schematically illustrates examples of prior art headsets.
Figure 5B:
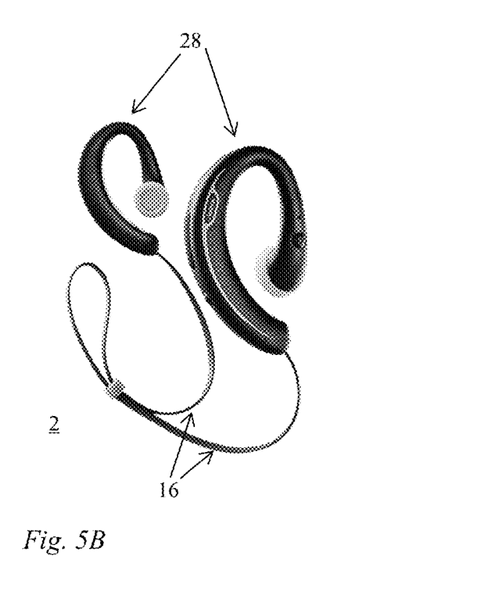

FIGS. 5A-5B schematically illustrates examples of prior art headsets.

FIG. 5A shows a headset 2 comprising two earpieces 4. Each earpiece 4 comprises a heart rate measurement unit 6 for measuring the heart rate in and/or at the ear of the user. Each earpiece 4 comprises an earwing unit 12 for securing and/or retaining the earpieces in the ears of the user. Each speaker unit comprises a replaceable eargel unit 14. The headset 2 comprises a wire 16 for connecting the two earpieces 4.

FIG. 5B shows a headset 2 comprising two earhook parts 28. The headset 2 comprises a wire 16 for connecting the two earhook parts 28.

Figure 6:
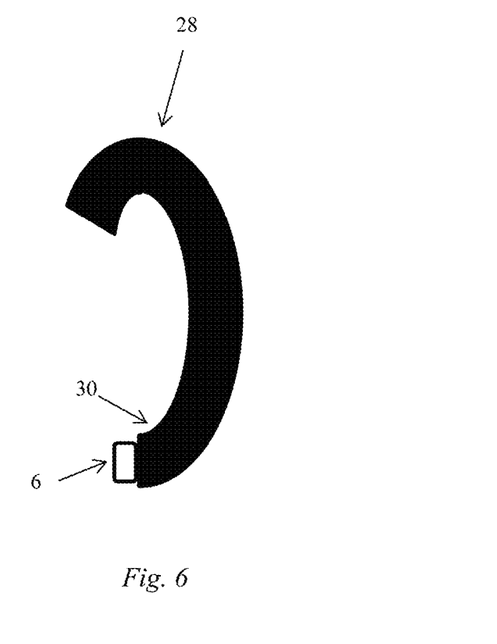
FIG. 6 schematically illustrates an example of an earhook of a headset.

FIG. 6 schematically illustrates an example of an earhook 28 of the headset (not shown), where the earhook is configured to be arranged at least partly around the outer ear of the user. The heart rate measurement unit 6 is arranged in a first end 30 of the earhook 28, where the first end 30 is configured to be arranged behind the ear of the user, when the user is wearing the headset during use.

Although particular features have been shown and described, it will be understood that they are not intended to limit the claimed invention, and it will be made obvious to those skilled in the art that various changes and modifications may be made without departing from the spirit and scope of the claimed invention. The specification and drawings are, accordingly to be regarded in an illustrative rather than restrictive sense. The claimed invention is intended to cover all alternatives, modifications and equivalents.

LIST OF REFERENCES 2 headset
4 earpiece
6 heart rate measurement unit
8 receiving member
10 detachable speaker unit
12 earwing unit
14 eargel unit
16 wire
18 membrane
20 second electrical connection parts of the speaker unit
22 first electrical connection parts of the receiving member
24 microphone
26 housing
28 earhook
30 first end of earhook

The invention claimed is:

1. A headset comprising a first earpiece, where the earpiece is configured to be arranged at least partly in an ear of a user, where the earpiece comprises:
   a heart rate measurement unit for measuring the heart rate at the ear of the user;
   a receiving member configured for accommodating a detachable speaker unit of the headset; and
   a detachable speaker unit which is configured to be attached and detached from the receiving member of the earpiece, and configured to be usable separately from the receiving member;
   wherein the receiving member has an inner periphery which includes a plurality of first electrical connectors spaced around the inner periphery and wherein the speaker unit includes an outer periphery with second electrical connectors spaced around said outer periphery, and wherein the inner periphery and outer periphery are sized to engage and maintain the receiving member and speaker unit mechanically engaged while said first and second electrical connectors are aligned and electrically engaged.

2. The headset according to claim 1, wherein the first and second electrical connectors are spaced around their respective peripheries so that they align and connect when said receiving member and speaker unit are brought together.

3. The headset according to claim 1, wherein the second electrical connectors on said speaker unit extend radially from the periphery.

4. The headset according to claim 1, wherein the heart rate measurement unit is located on said receiving member and is electrically detachable from said speaker unit when said speaker unit is removed.

5. The headset according to claim 1, wherein the receiving member includes a microphone and wherein the heart rate measurement unit and microphone are located on said receiving member and are electrically separable from said speaker unit when said speaker unit is removed.

6. The headset according to claim 1, wherein an inner periphery of the receiving member comprises electrical connectors which are configured to be arranged facing each other, when the speaker unit is attached in the receiving member thereby providing an electrical connection between the speaker unit and the earpiece.

7. The headset according to claim 6, wherein at least two of the electrical connectors on the receiving member and at least two of the electrical connectors on the speaker unit are arranged to be rotationally symmetrical.

8. The headset according to claim 6, wherein the electrical connectors on the receiving member and the electrical connectors on the speaker unit are spaced equidistant around the respective peripheries and are arranged to be rotationally symmetrical.

9. The headset according to claim 1, wherein the earpiece comprises an earwing unit for retaining the earpiece in the ear of the user.

10. The headset according to claim 1, wherein the speaker unit comprises a replaceable eargel unit.

11. The headset according to claim 1, wherein the receiving member is formed at least in part, of a membrane capable of transmitting air and sound therethrough.

12. The headset according to claim 1, wherein the heart rate measurement unit is arranged in a first end of an earhook configured to be arranged behind the ear of the user.

13. The headset according to claim 1, wherein the earpiece comprises a microphone, and wherein the microphone is arranged in a housing of the earpiece.

14. The headset according to claim 1, wherein the earpiece comprises a microphone, and wherein the microphone is arranged in the speaker unit.

15. An earpiece for use in a headset, where the earpiece is configured to be arranged at least partly in an ear of a user, where the earpiece comprises:
- a heart rate measurement unit for measuring the heart rate at the ear of the user;
- a microphone;
- a receiving member configured for accommodating a detachable speaker unit of the headset; and
- a detachable speaker unit which is configured to be attached and detached from the receiving member of the earpiece said heart rate measurement unit and said microphone being located on said receiving member and electrically connected and electrically detachable from said speaker unit when said receiving member and speaker unit are separated from each other.

\* \* \* \* \*